(12) United States Patent
Richart et al.

(10) Patent No.: US 11,883,556 B2
(45) Date of Patent: Jan. 30, 2024

(54) METHOD FOR SURFACE TREATMENT OF A BIO-COMPATIBLE METAL MATERIAL AND IMPLANT TREATED BY SAID METHOD

(71) Applicant: SELENIUM MEDICAL, La Rochelle (FR)

(72) Inventors: Olivier Richart, Lagord (FR); Herve Depery, Annecy le Vieux (FR)

(73) Assignee: SELENIUM MEDICAL, La Rochelle (FR)

( * ) Notice: Subject to any disclaimer, the term of this patent is extended or adjusted under 35 U.S.C. 154(b) by 28 days.

(21) Appl. No.: 17/306,168

(22) Filed: May 3, 2021

(65) Prior Publication Data

US 2021/0252187 A1    Aug. 19, 2021

Related U.S. Application Data

(62) Division of application No. 16/090,999, filed on Oct. 3, 2018, now Pat. No. 11,058,794.

(51) Int. Cl.

| | |
|---|---|
| *A61L 27/06* | (2006.01) |
| *A61C 13/00* | (2006.01) |
| *C23F 1/38* | (2006.01) |
| *C23F 1/26* | (2006.01) |
| *B24C 1/00* | (2006.01) |

(Continued)

(52) U.S. Cl.
CPC .......... *A61L 27/06* (2013.01); *A61C 8/0012* (2013.01); *A61C 8/0013* (2013.01); *A61C 13/0007* (2013.01); *A61L 27/50* (2013.01); *A61L 27/56* (2013.01); *B24C 1/00* (2013.01); *C23F 1/26* (2013.01); *C23F 1/38* (2013.01);

*A61L 27/042* (2013.01); *A61L 2400/12* (2013.01); *A61L 2400/18* (2013.01); *A61L 2430/02* (2013.01); *A61L 2430/12* (2013.01); *B24C 11/00* (2013.01)

(58) Field of Classification Search
CPC .......... A61L 27/06; A61C 8/0012; A61F 2/28
See application file for complete search history.

(56) References Cited

U.S. PATENT DOCUMENTS

| | | |
|---|---|---|
| 2009/0132048 A1 | 5/2009 | Denzer |
| 2010/0010632 A1 | 1/2010 | Bourges et al. |
| | (Continued) | |

FOREIGN PATENT DOCUMENTS

| | | |
|---|---|---|
| CN | 104451684 | 3/2015 |
| WO | 2006066936 A | 6/2006 |
| WO | 2013124693 | 8/2013 |

OTHER PUBLICATIONS

International Search Report dated Jun. 6, 2017.
CN Office Action dated Dec. 17, 2020.

*Primary Examiner* — Dah-Wei D. Yuan
*Assistant Examiner* — Andrew J Bowman
(74) *Attorney, Agent, or Firm* — IPSILON USA, LLP

(57) ABSTRACT

A biocompatible metal implant is provided with a treated surface subject to abrasive mechanical treatment, acid treatment, and sodium treatment, where the biocampatible metal implant treated surface has a macroporosity in the form of cells having dimensions of the order of 50 μm to 250 μm, the cells having pores of from 1 μm to 50 μm, and pores with a size of less than a micrometer, homogeneously over the whole of the treated surface, the treated surface having a surface roughness Ra of greater than or equal to 1.90 μm.

3 Claims, 3 Drawing Sheets

(51) Int. Cl.
  *A61L 27/56* (2006.01)
  *A61L 27/50* (2006.01)
  *A61C 8/00* (2006.01)
  *B24C 11/00* (2006.01)
  *A61L 27/04* (2006.01)

(56) References Cited

U.S. PATENT DOCUMENTS

2010/0185299 A1* 7/2010 Nies .......................... A61F 2/28
  623/23.6
2010/0243429 A1  9/2010 Aoki et al.
2011/0171602 A1  7/2011 Schlottig
2011/0233169 A1  9/2011 Mayfield

* cited by examiner

METHOD FOR SURFACE TREATMENT OF A BIO-COMPATIBLE METAL MATERIAL AND IMPLANT TREATED BY SAID METHOD

RELATED APPLICATION

This application is a divisional application of U.S. patent application Ser. No. 16/090,999, filed on Oct. 3, 2018 which in turn is a National Phase of PCT/FR2017/050795, filed on Apr. 5, 2017, which claims the benefit of priority from French Patent Application No. 16 53094, filed on Apr. 8, 2016, the entirety of which are incorporated by reference.

FIELD OF THE INVENTION

The present invention relates to the field of biocompatible materials, and more particularly the field of implants, especially dental or spinal implants.

It relates in particular to a process for preparing and treating the surface of such a material.

PRIOR ART

Currently, dental implants, devices intended to be partially inserted into the jaw of a patient with a view to replacing a tooth, are generally made from metal alloys. These alloys usually contain titanium, for reasons of strength. The same applies to spinal implants.

With a view to promoting the osseointegration of an implant, either the application of coatings comprising calcium phosphate (in the form for example of hydroxyapatite, having a chemical nature similar to that of bone) or surface treatments in order to increase both the surface roughness thereof and the hydrophilic nature thereof have been proposed.

Current surface treatments usually comprise a sandblasting of said surface using alumina grains, and/or treatment with an acid solution (inorganic acids such as hydrofluoric acid, hydrochloric acid, sulfuric acid, phosphoric acid, nitric acid, etc. or a mixture of several of these acids).

An alloy based on titanium, aluminum and vanadium, for medical use, has recently been commercialized: it is TA6V ELI (Extra Low Interstitial).

However, the current surface treatments for this TA6V ELI alloy, which are intended to create a macroporosity and a microporosity at the surface, are not satisfactory for the following reasons:

- to create surface macroporosity, the sandblasting treatments with alumina particles (inexpensive and very hard particles) leave alumina microbeads encrusted on the surface of the material,
- a subsequent treatment with hydrofluoric acid may remove them, but weakens the material and degrades its mechanical properties;
- to create microporosity, use is then made of acid attacks by means of solutions of hydrochloric acid, and/or solutions combining hydrofluoric acid and nitric acid, which attack the surface of the material leaving protrusions or de-encrusting vanadium atoms.

Neither the presence of alumina impurities, nor the vanadium atoms at the surface are desired by practitioners. Specifically, in the dental field, each impurity may be a cause of failure of the osseointegration of an implant.

Thus the drawback of the TA6V ELI alloy is the presence of vanadium (4% by weight) and aluminum (6% by weight) in its composition. These two elements, which are not biocompatible, may impair the biological properties of the implants made from this material.

OBJECTIVES OF THE INVENTION

A first objective of the present invention is therefore to overcome the drawbacks of the above processes and to provide a process for the surface treatment of a biocompatible metal material, such as an implant, which increases the surface roughness without leaving residues that may slow down the osseointegration of said material.

Another objective of the invention is to provide a surface treatment process that can be adapted to the TA6V ELI alloy based on titanium, aluminum and vanadium, for medical use.

Another objective of the invention is also to provide a process for the surface treatment of a biocompatible material, such as an implant, which increases the hydrophilic nature of its surface.

DETAILED DESCRIPTION

For this purpose, the present invention relates to a process for the surface treatment of a biocompatible metal material, such as an implant, comprising the following consecutive steps:

i) abrasive mechanical treatment of the surface of said material by means of a mixture of abrasive grains based on calcium phosphate, such as hydroxyapatite and/or tricalcium phosphate;

ii) acid treatment by soaking, at a temperature above 40° C., said material in a bath comprising sulfuric acid and hydrochloric acid, followed by at least one rinse, preferably two rinses, with demineralized water;

iii) sodium treatment by soaking, at a temperature above 40° C., said material in a sodium hydroxide-based bath followed by at least one rinse, preferably two rinses, with demineralized water and by hot air drying.

The main advantage of this process is to use, for the so-called "sandblasting" step, i.e. the abrasive mechanical treatment step, grains consisting of hydroxyapatite and tricalcium phosphate, which are constituent materials of the structure of the bone. If residues remain present at the surface, they do not constitute impurities, but may on the contrary participate in the osseointegration of the material.

To date, such a mechanical treatment using hydroxyapatite and tricalcium phosphate grains had only been carried out for surfaces made of polymer material (FR 2 906 147). However, surprisingly, the abrasive mechanical treatment using calcium phosphate grains, such as a mixture of hydroxyapatite and tricalcium phosphate grains, carried out by high-pressure projection of said abrasive grains, makes it possible to create, at the surface of a metal material, such as a material made of titanium alloy, macroporosities at the surface of said material in the form of cells having dimensions of the order of 50 μm to 250 μm.

Hot treatments, at a temperature above 40° C., in respectively acid and sodium media then make it possible to create a microporosity (pores of the order of 1 to 50 μm) and also a nanoporosity (pores with a size of less than a micrometer) in said first cells, homogeneously over the whole of the treated surface.

The first anchoring of the implant takes place owing to the surface macroporosity of the material; the microporosity helps to promote the creation of secondary anchoring bridges or tentacles, and finally the nanoporosity produces a suction effect (capillary action) increasing the vascularization of this graft, and therefore the osseointegration thereof.

Preferably, the biocompatible material is a titanium alloy, more particularly an alloy based on titanium, aluminum and vanadium, such as the alloy known as TA6V ELI (according to the standard ASTM F136).

Indeed it has been observed, surprisingly, that the combination of the steps of the surface treatment process, according to the present invention, applied to the TA6V ELI alloy makes it possible to create a very rough hydrophilic surface without revealing detachable vanadium crystals or leaving residues of undesirable abrasive materials at the surface of the implants.

According to advantageous features of the invention:

The mixture of the hydroxyapatite and tricalcium phosphate grains comprises from 80% to 90% of hydroxyapatite and from 10% to 20% of tricalcium phosphate.

The hardness of these grains is preferably greater than 350 Hv (Vickers hardness).

The abrasive grains of calcium phosphate, in particular of hydroxyapatite and tricalcium phosphate, have a particle size of between 160 and 400 micrometers, preferably between 200 and 360 micrometers.

The acid bath comprises from 45% to 55% by volume of 95% sulfuric acid and from 45% to 55% by volume of 37% hydrochloric acid.

The acid treatment is carried out by soaking said material in a bath at a temperature between 60° C. and 70° C. for a duration of from 18 to 30 minutes, preferably from 20 to 25 minutes.

The sodium treatment is carried out by soaking said material in sodium hydroxide at a molar concentration of 4 to 6 M and at a bath temperature of between 60° C. and 70° C. for a duration of between 18 and 30 minutes, preferably between 20 and 25 minutes.

The treatments in the acid and sodium baths are advantageously carried out with stirring, and are carried out immediately one after the other in the order indicated above.

The present invention also relates to an implant that has undergone a surface treatment by means of the process described above, characterized in that its surface has a macroporosity in the form of cells having dimensions of the order of 50 μm to 250 μm, said cells comprising pores of from 1 μm to 50 μm, and pores with a size of less than a micrometer, homogeneously over the whole of the treated surface, said treated surface having a surface roughness Ra of greater than or equal to 1.90 μm.

The implant according to the invention that has undergone a surface treatment by means of the process described above is also characterized in that the contact angle of the treated surface is less than or equal to 10° in the presence of distilled water or ethylene glycol as wetting agent. This hydrophilic nature of the surface thus increases the capillary action in the pores of the surface of the material, in particular for physiological liquids.

The implant according to the invention may also be an implant made of an alloy of titanium, aluminum and vanadium, such as the alloy known as TA6V ELI, characterized in that it has undergone a surface treatment by means of the process described above, its treated surface having contents of aluminum and vanadium that are reduced by at least 30% relative to the initial alloy, measured by EDS (Energy Dispersive Spectroscopy) analysis.

The surface treatment according to the invention is suitable for implants that have a threaded outer surface.

BRIEF DESCRIPTION OF THE DRAWINGS

The invention will be clearly understood on reading the following description of an exemplary embodiment, with reference to the appended drawings, in which.

DETAILED DESCRIPTION

Example 1 According to the Invention

Figure 1:
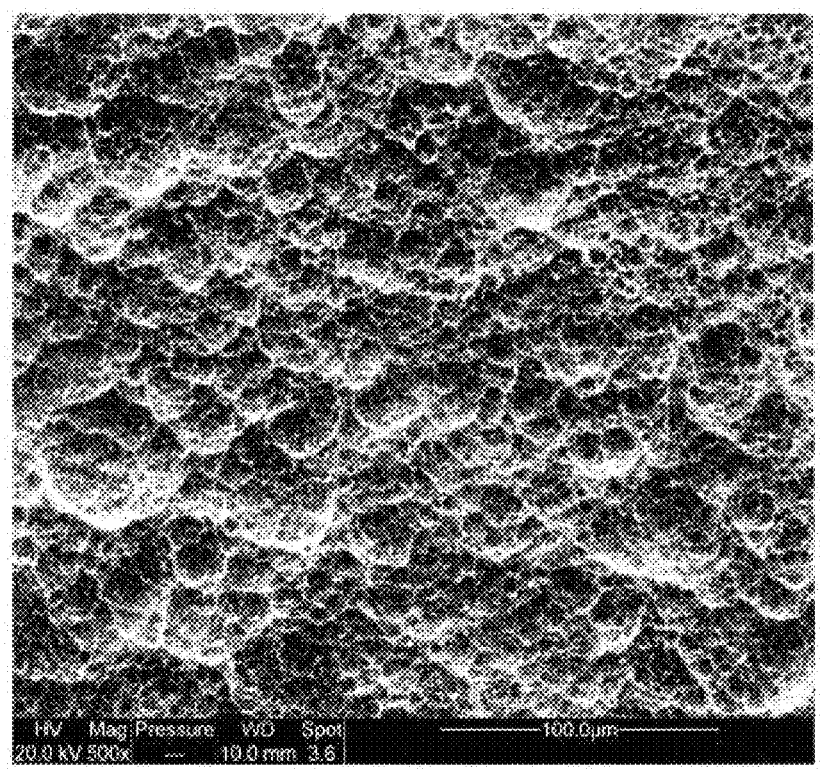
FIG. 1 is a scanning electron microscopy image, with a magnification of 500, of the surface of an implant treated according to the process of the present invention.
Figure 2:
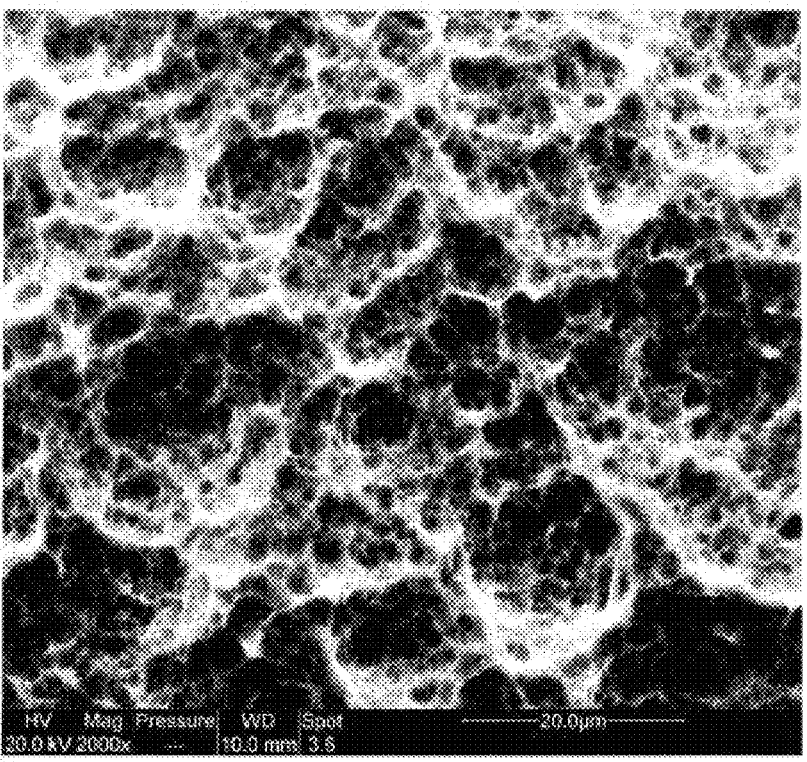
FIG. 2 is an image of the surface of the implant from FIG. 1 with a magnification of 2000.
Figure 3:
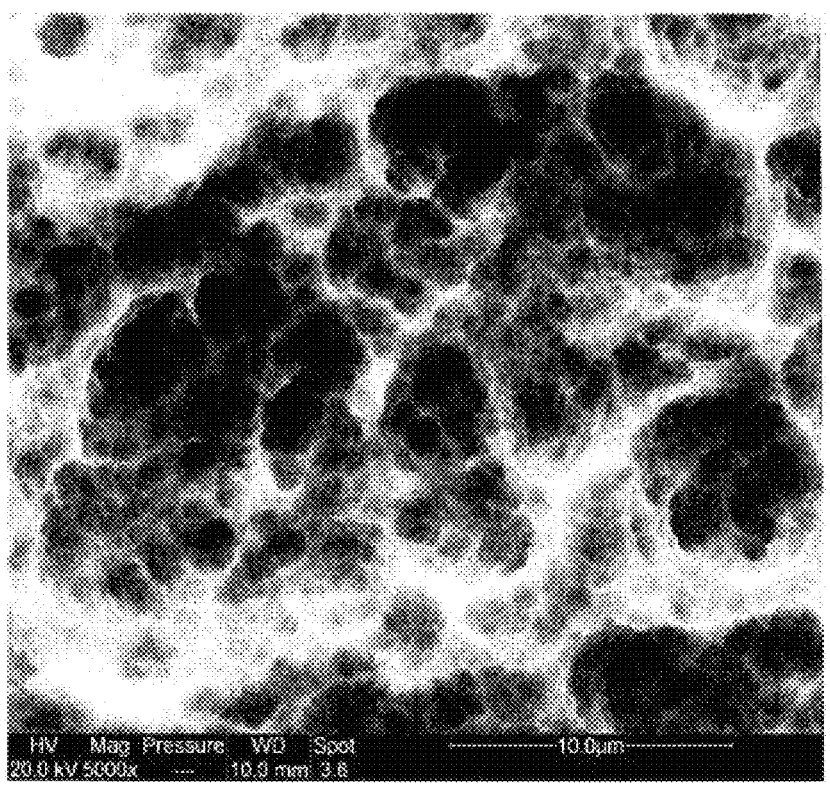
FIG. 3 is an image of the surface of the implant from FIG. 1 with a magnification of 5000.
Figure 4:
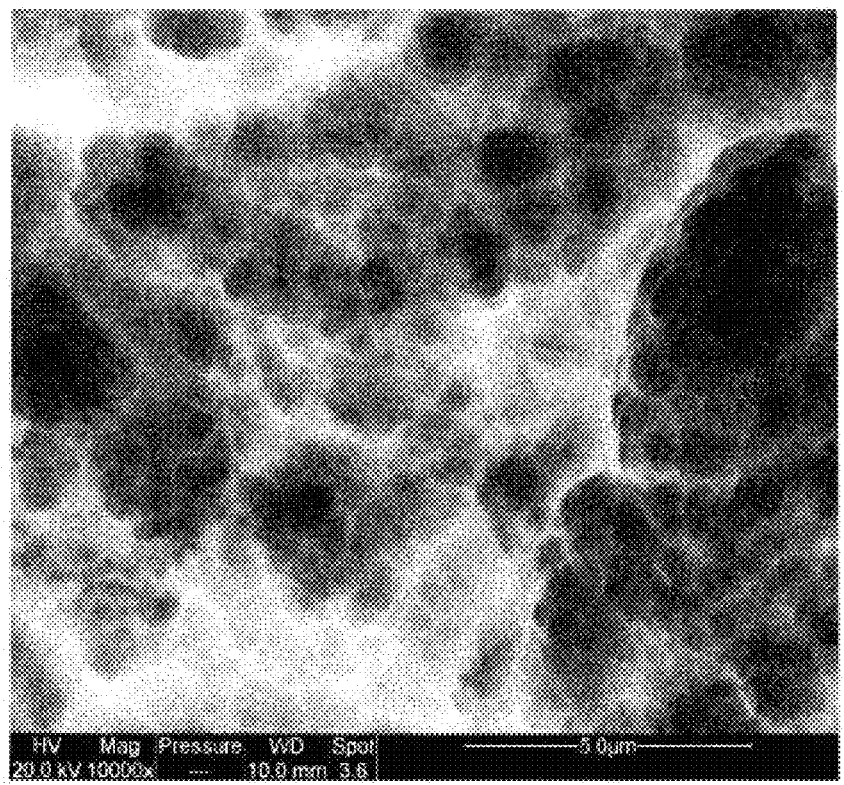
FIG. 4 is an image of the surface of the implant from FIG. 1 with a magnification of 10 000.
Figure 5:
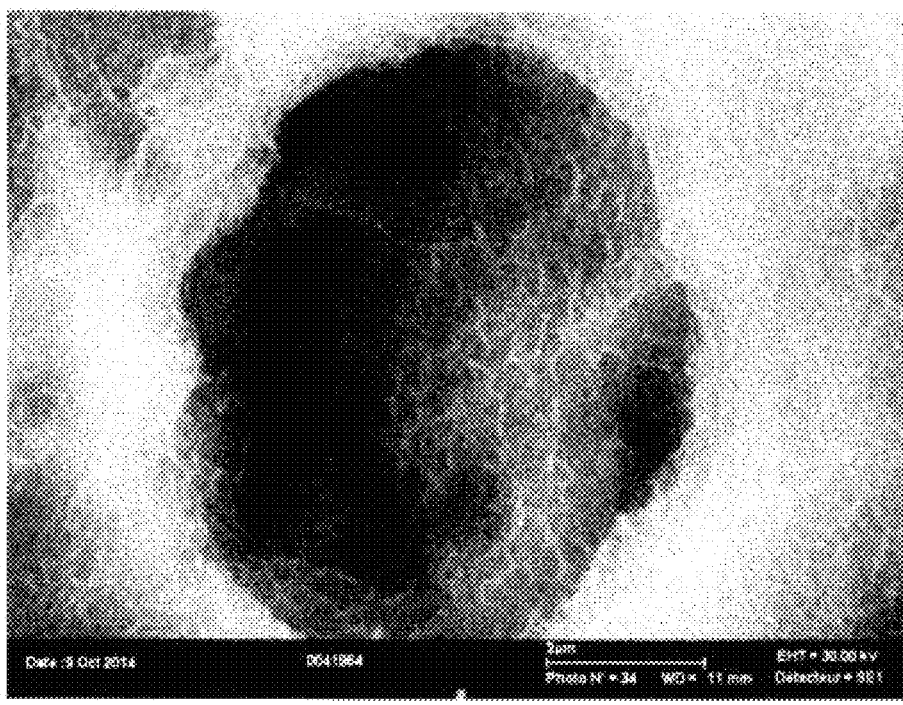
FIG. 5 is an image of the surface of the implant from FIG. 1 with a magnification of 30 000.

The surface treatment of an implant made of TA6V ELI alloy (according to the standard ASTM F136, a titanium-based alloy containing 6% by weight of aluminum and 4% by weight of vanadium: see table 1) is carried out according to a treatment known as "nano-etching" in three consecutive steps, described in detail below.

TABLE 1

| Fe max. % | O max. % | N max. % | C max. % | H max. % | Al % | V % |
|---|---|---|---|---|---|---|
| 0.25 | 0.13 | 0.05 | 0.08 | 0.012 | 5.50-6.50 | 3.50-4.50 |

Step 1: Mechanical Treatment

The implants are sandblasted with an abrasive composed of hydroxyapatite (85%±5%) and tricalcium phosphate (15%±5%) having a Vickers hardness equal to 532 Hv, having a diameter of the powder grains of between 160 and 400 μm, with a predominance of grains having a size of between 200 and 360 μm in diameter.

This step consists in creating porosities having a size ranging up to 250 μm in diameter.

The grains of abrasives are projected using a nozzle positioned at around 10 to 20 cm from the surface of the implant under a pressure of from 5 to 7 bar for 60±10 seconds.

Step 2: Acid Treatment

This step consists in creating porosities of several tens of microns in diameter and in depth homogeneously over the entire surface treated.

The treatment is carried out in a mixture composed of two acids. The acid composition and the treatment parameters are described below:
  composition of the bath: 50%±5% by volume of 95% sulfuric acid and 50%±5% by volume of 37% hydrochloric acid,
  treatment temperature: 67±2.5° C.,
  treatment time: 22±1 min,
  with stirring of the bath.

A longer treatment time or a temperature above the range indicated results in an attack of the macro-roughness created in step 1.

Step 3: Sodium Treatment

The objective of this treatment is to create a tissue of nanometer-size porosity at the surface of the implant.

This step is carried out in a sodium hydroxide bath, as follows:
- composition of the bath: 5±0.5 M (5±0.5 mol/L) sodium hydroxide,
- bath temperature: 67±2.5° C.,
- treatment time: 22±1 min,
- stirring of the bath.

An insufficient sodium treatment (insufficient NaOH concentration, for instance of less than 4 mol/L, lower temperature or shorter treatment time) leads to surfaces that are less hydrophilic with contact angles in the presence of distilled water, ethylene glycol or diiodomethane of greater than 50°, or even greater than 70°, and also to an insufficient nanoporosity.

Results of SEM Observations:

The images obtained by observation with the scanning electron microscope, presented in FIGS. 1 to 5 at various magnifications (respectively 500, 2000, 5000, 10 000 and 30 000), reveal a very uneven and very rough surface.

The surface has, specifically, an appearance with porosities of several tens of microns in diameter which themselves comprise porosities of several microns in diameter and in depth. These same microporosities also comprise porosities having a diameter and a depth of less than a micron, namely several hundred nanometers. The presence of this triple level of porosity at the surface of the material constitutes a significant advantage for the osseointegration of the implant.

It is even possible to observe, on the SEM image with a magnification of 30 000, a tissue of very fine fibers that covers the entire treated surface.

EDS analyses (Energy Dispersive Spectroscopy analyses, carried out under vacuum with a FEI QUANTA 200 machine) of this surface reveal a strong presence of titanium and of oxygen (therefore probably of titanium oxide), as presented in table 2 below which compares the chemical composition of the treated surface and that of the crude alloy before treatment.

TABLE 2

| Elements | Composition by weight (%) | |
|---|---|---|
| | Alloy with treated surface | Crude alloy |
| Titanium | 66.15 | 86.95–89.20 |
| Oxygen | 26.11 | 0.5 |
| Aluminum | 3.50 | 5.5–6.75 |
| Vanadium | 1.92 | 3.5–4.5 |
| Carbon | 1.44 | 0.08 |
| Sodium | 0.11 | — |
| Iron | — | 0.4 |
| Hydrogen | — | 0.015 |

The surface of the alloy treated according to the invention has lower contents of aluminum and of vanadium than those present at the surface of a crude grade 23 (TA6V ELI) titanium alloy. These analyses also demonstrate the strong presence of oxygen at the surface of the treated implant, which means that there is formation of a titanium oxide layer.

Comparative Example 2

A surface treatment of an implant made of Straumann SLA® titanium-based alloy is carried out according to the same three steps and under conditions identical to those of example 1 above.

Roughness Measurements:

The results of the Ra and Rz roughness measurements (carried out using a MITOTOYO SJ400 machine) comparing the surfaces of the implants treated according to example 1 and comparative example 2 are presented in table 3 below.

The meanings of Ra and Rz are the following:

"Ra": mean deviation. It is the arithmetic mean of the absolute values of the deviations, between the peaks and the valleys. "Ra" measures the distance between this mean and the "central line".

"Rz": regularity. It is the mean of the greatest difference in height between the highest point of a peak and the lowest bottom of a valley, observed over 5 lengths.

TABLE 3

| Surfaces tested | Ra | Rz | Comments |
|---|---|---|---|
| Example 1 | 1.90 μm | 10.46 μm | The surface of the implant from example 1 is rougher than that of the implant from example 2 |
| Example 2 (Comp.) | 1.83 μm | 10.03 μm | |

Figure 6:
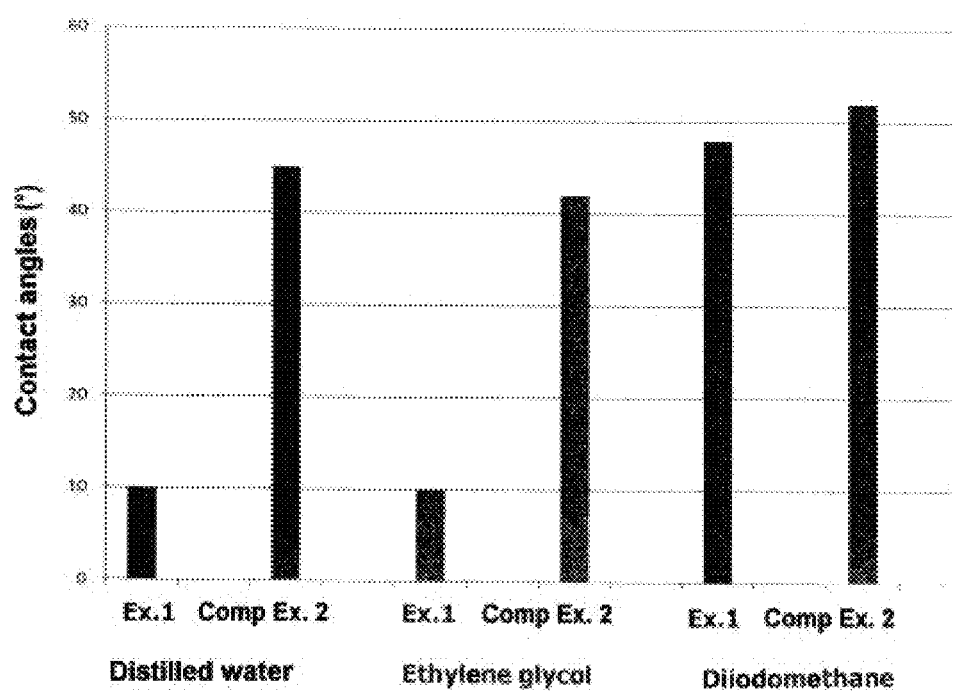
FIG. 6 is a chart comparing the contact angles of the implant surfaces from examples 1 and 2 measured with various wetting agents.

Contact Angle Measurements:

Contact angle measurements were carried out with three different liquids (distilled water, ethylene glycol and diiodomethane) for the implants from examples 1 and 2. The results, presented in FIG. 6, show significant differences when the wetting agent is either distilled water or ethylene glycol, demonstrating a much greater hydrophilic nature for the surface treated according to the process of the present invention.

The invention claimed is:

1. A biocompatible metal implant made of an alloy of titanium, aluminum and vanadium comprising:
   at least one treated surface, said treated surface subject to abrasive mechanical treatment of the surface of said material by means of abrasive grains based on calcium phosphate;
   said treated surface subject to acid treatment by soaking, at a temperature above 40° C., said material in a bath comprising sulfuric acid and hydrochloric acid, followed by at least one rinse with demineralized water; and
   said treated surface subject to sodium treatment by soaking, at a temperature above 40° C., said material in a sodium hydroxide-based bath having only sodium hydroxide, followed by at least one rinse with demineralized water and by hot air drying,
   wherein said biocampatible metal implant treated surface has a macroporosity in the form of cells having dimensions of the order of 50 μm to 250 μm, said cells comprising pores of from 1 μm to 50 μm, and pores with a size of less than a micrometer, homogeneously over the whole of the treated surface, said treated surface having a surface roughness Ra of greater than or equal to 1.90 μm, and
   wherein said biocompatible metal implant has undergone a surface treatment, said treated surface of said biocompatible metal implant having contents of aluminum and vanadium that are reduced by at least 30% relative to the initial alloy, measured by EDS analysis.

2. The biocompatible metal implant as claimed in claim 1, wherein the contact angle of the treated surface is less than or equal to 10° in the presence of distilled water or ethylene glycol as wetting agent.

3. The biocompatible metal implant as claimed in claim 1, wherein said alloy of titanium, aluminum and vanadium is the alloy known as TA6V ELI.

\* \* \* \* \*